United States Patent [19]

Sanderson et al.

[11] Patent Number: 5,241,112
[45] Date of Patent: Aug. 31, 1993

[54] PREPARATION OF TRIALKYLACETIC ACIDS, PARTICULARLY OF PIVALIC ACID, USING SOLID ACID CATALYSIS

[75] Inventors: William A. Sanderson, Portola Valley; Michael A. Richard, Foster City, both of Calif.

[73] Assignee: Catalytica, Inc., Mountain View, Calif.

[21] Appl. No.: 682,810

[22] Filed: Apr. 9, 1991

[51] Int. Cl.$^5$ .................. C07C 51/14; A23F 7/00
[52] U.S. Cl. ........................... 562/521; 554/83
[58] Field of Search ............... 562/521; 260/413, 408, 260/400, 403, 404; 554/92, 96, 97, 80, 83, 78, 69, 63, 110, 118, 119, 159, 129, 132, 154

[56] References Cited

U.S. PATENT DOCUMENTS

| | | | |
|---|---|---|---|
| 2,831,877 | 4/1958 | Koch et al. | 260/413 |
| 2,967,873 | 1/1961 | Koch et al. | 260/410.9 |
| 3,036,124 | 5/1962 | John, Jr. | 562/521 |
| 3,059,004 | 10/1962 | Waale et al. | 562/521 |
| 3,061,621 | 10/1962 | Koch et al. | 260/443 |
| 3,068,256 | 12/1962 | Roming | 260/413 |
| 3,527,779 | 9/1970 | Paulis et al. | 260/443 |
| 4,232,146 | 11/1980 | DiGiacomo et al. | 528/395 |
| 4,235,990 | 11/1980 | DiGiacomo et al. | 528/287 |
| 4,235,991 | 11/1980 | DiGiacomo et al. | 528/391 |
| 4,256,872 | 11/1980 | DiGiacomo et al. | 528/395 |
| 4,256,913 | 3/1981 | Jung et al. | 562/521 |
| 4,262,138 | 4/1981 | Gelbein | 560/233 |
| 4,267,308 | 5/1981 | Parziale | 528/395 |
| 4,276,409 | 6/1981 | DiGiacomo et al. | 528/362 |
| 4,276,410 | 6/1981 | DiGiacomo et al. | 528/373 |
| 4,276,411 | 6/1981 | DiGiacomo et al. | 528/395 |
| 4,298,723 | 11/1981 | DiGiacomo et al. | 528/271 |
| 4,299,943 | 11/1981 | DiGiacomo et al. | 528/9 |
| 4,311,851 | 1/1982 | Jung et al. | 560/233 |
| 4,373,079 | 2/1983 | Parziale et al. | 528/9 |
| 4,384,981 | 5/1983 | Dines et al. | 564/305 X |
| 4,386,013 | 5/1983 | Callahan et al. | 260/429 X |
| 4,390,690 | 6/1983 | DiGiacomo et al. | 260/429 X |
| 4,429,111 | 1/1984 | Dines et al. | 528/395 |
| 4,436,899 | 3/1987 | DiGiacomo | 528/395 |
| 4,868,343 | 9/1989 | King et al. | 568/697 |

FOREIGN PATENT DOCUMENTS

| | | |
|---|---|---|
| 0249976 | 12/1987 | European Pat. Off. |
| 998974 | 7/1965 | United Kingdom ........... 562/521 |
| 1167116 | 10/1969 | United Kingdom . |
| 1174209 | 12/1969 | United Kingdom . |

*Primary Examiner*—José G. Dees
*Assistant Examiner*—Joseph M. Conrad, III
*Attorney, Agent, or Firm*—Morrison & Foerster

[57] ABSTRACT

This invention is a process for the production of trialkyl acetic acids, particularly of pivalic acid, from branched olefins, particularly isobutene, and carbon monoxide using a solid acid catalyst and optionally with minor amounts of a Lewis acid such as boron trifluoride.

17 Claims, No Drawings

PREPARATION OF TRIALKYLACETIC ACIDS, PARTICULARLY OF PIVALIC ACID, USING SOLID ACID CATALYSIS

FIELD OF THE INVENTION

This invention is a process for the production of trialkyl acetic acids, particularly of pivalic acid, from branched olefins, particularly isobutene, and carbon monoxide using a solid acid catalyst and optionally with minor amounts of a Lewis acid such as boron trifluoride.

BACKGROUND OF THE INVENTION

Of the trialkylacetic acids, pivalic acid [$(CH_3)_3CCOOH$] is one of the most widely used. It is a fine chemical suitable as a starting material for various agrichemicals, pharmaceuticals, aroma chemicals, specialty chemicals, and polymer additives. Trialkylcarboxylic acids are typically made in large scale commercial amounts using a non-catalytic process involving substantial amounts of highly corrosive liquid acidic reactant, often containing boron trifluoride. The acidic reactants are typically present in molar amounts equal to or greater than that of the branched olefin feed.

Typical of this technology is U.S. Pat. No. 3,068,256 to Roming. This patent describes a process where the material characterized as the catalyst (liquid mineral acids having a specific gravity greater than 1.25, e.g., $H_2SO_4$, $BF_3 2H_2O$, or mixtures of $BF_3 2H_2O$ with $H_2SO_4$ or $H_3PO_4$) is used in amounts approximately stoichiometric with the olefinic feed. However, this catalytic material must be recovered by hydrolysis of an intermediate complex generated by stoichiometric reaction of olefin, carbon monoxide, and the acid. Consequently, the disclosed process requires a large catalyst inventory; it also requires expensive materials of construction suitable for handling that large corrosive acid catalyst inventory. Furthermore, the hydrolysis step is very difficult to control if optimal regeneration of the acid catalyst of its most active state is desired.

In summary, the process disclosed in the Roming patent is not truly catalytic in nature in the sense that large amounts of the acid along with the feed olefin, carbon monoxide, and water are reacted to form the product carboxylic acid. The catalyst separation and recovery steps are complex.

Similarly, U.S. Pat. No. 3,061,621 to Koch et al., discloses a process for the production of carboxylic acids from olefins and carbon monoxide using a molar excess of an acid catalyst selected from orthophosphoric acid, derivatives of orthophosphoric acid, higher polyphosphoric acids, and their mixtures. This process involves use of large amounts of the catalyst which must be regenerated and recycled in a complicated series of steps.

The process shown in U.S. Pat. No. 2,831,877 to Koch et al., involves two separate steps. In the first step, feed olefin and carbon monoxide are contacted with very strong, and potentially very corrosive, acid catalysts. Suitable acids are said to include 90% to 100% sulfuric acid, anhydrous HF, anhydrous HF-$BF_3$, chlorosulfonic acid, and fluorosulfonic acid. The resulting intermediate formed upon stoichiometric reaction of the acid, olefin, and carbon monoxide is hydrolyzed with water to liberate the product carboxylic acid. The catalyst must be regenerated to its anhydrous form prior to re-use in the process. This step entails treatment of a very corrosive stream containing significant amounts of water. Clearly, costly corrosion-resistant materials of construction are necessary. A preferable process would entail the use of a catalyst having a substantially less corrosive catalyst and a more economical catalyst recovery step.

A further U.S. patent to Koch et al. (U.S. Pat. No. 2,967,873) describes a process for the production of alkyl esters of carboxylic acids. The process involves two steps. This first step involves reaction of an olefin (containing at least six carbon atoms) with carbon monoxide using approximately a stoichiometric amount of an acid catalyst. The acid catalyst is said to contain boron trifluoride in the form of hydroxy- and alkoxyfluoboric acid, potentially with complexed alcohols. The second step is the alcoholysis of the intermediate complex formed in the first step to produce the desired ester.

A process suffering from a highly corrosive operating environment and requiring a large excess of wet hydrofluoric acid (as the catalyst) is disclosed in GB 1,167,116 assigned to Shell Internationale Research Maatschappij N.V. The process involves the one-step synthesis of carboxylic acids by reacting a branched $C_{4-10}$ olefin with carbon monoxide in the presence of a large excess of hydrofluoric acid (preferably a hydrogen fluoride/olefin ratio of about 10:1) and about a 50% molar excess of water. As with a number of processes discussed above, this process has a serious disadvantage in that the hydrofluoric acid must be separated from a product mixture which contains excess water. Hydrofluoric acid is also extremely corrosive and toxic.

A process similar to that disclosed in GB 1,167,116 is shown in GB 1,174,209 also assigned to Shell. GB '209 also discloses steps for recovery and recycle of at least a portion of the hydrofluoric acid catalyst.

Another process using an acid catalyst in an amount more than equimolar to the olefin feed is found in U.S. Pat. No. 3,527,779 to Paulis et al. That process uses a boron trifluoride-water phosphoric acid catalyst which is said to be less corrosive than hydrofluoric acid or boron trifluoride hydrate and more readily recovered from the carboxylic acid product. The catalyst is, however, used in molar excess to the feed olefin. It may be recovered in a subsequent step for recycle.

Much of the literature discussed here is limited to the reaction of higher olefins to produce saturated carboxylic acids. In U.S. Pat. No. 4,256,913 to Jung et al. the disclosed process is limited to the carbonylation of lower non-branched olefins, ethylene and propylene, to the corresponding carboxylic acids. A description for the recovery and reuse of the catalyst is not shown.

The U.S. Pat. No. 4,311,851 to Jung et al. discloses a process for producing carboxylic acid esters and for recovering and reconstituting the boron trifluoride-alcohol catalyst. This process involves a very complicated series of steps for recovery of the catalyst: the operation is carried out until one-half of the alcohol feed is consumed, any remaining free $BF_3$ is vaporized, additional alcohol is added to the reaction medium, and the reaction mixture is distilled. An azeotrope of the alcohol and the product ester is the distillation product. Heavy by-products are removed from the distillation bottoms by solvent extraction. The treated bottoms are mixed with added $BF_3$ to form the original catalyst mixture. A simpler process would be desirable.

The U.S. patent to Gelbein (U.S. Pat. No. 4,262,138) is a variation of the process shown in Jung et al. '851 (discussed above) but also appears to be specific to the carbonylation of ethylene and propylene.

A published European Patent Application (No. 0,249,976) assigned to BASF AG discloses a process for the production of carboxylic acids from the reaction of an olefin with carbon monoxide and water over a zeolite catalyst or a modified zeolite catalyst. This process uses a catalyst which is easy to handle and has low corrosivity. However, the process exemplifies high yields of carboxylic acids only at high temperatures and pressures.

Our process is one which uses solid acid catalysts optionally in combination with minor amounts of adjunct Lewis acids. None of the materials cited above utilize their "catalysts" in truly catalytic amounts in producing trialkylacetic acids.

SUMMARY OF THE INVENTION

This invention is a solid acid catalyzed process for producing certain trialkylacetic acids from corresponding branched olefins, carbon monoxide, and water according to the following reaction:

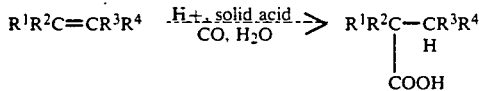

where $R^1$, $R^2$ = alkyl or substituted alkyl; $R^3$, $R^4$ = H, alkyl, or substituted alkyl. The solid acid catalyst is desirably a compound comprising sulfonic acid and phosphonic acid groups where the phosphonic acid groups are covalently bonded to a polymeric chain, where the resulting product is represented by the general formula:

$$M(O_3ZR)_n$$

where M is a tetravalent metal ion, Z is a pentavalent atom selected from the elements of Group V having atomic weights greater than 30, R is selected from substituted or non-substituted organo radicals and mixtures of substituted and unsubstituted organo radicals, and n varies from 1 to 2. The substituents of the "R" moiety may be fluorine, chlorine, bromine, iodine, or the like as well as sulfur, oxygen, or phosphorus but must contain an acid group. Particularly desirable "R" moieties include —$(CH_2)_mSO_3H$, —$C_6H_4SO_3H$, —$C_6H_4(SO_3H)_2$, —$(CF_2)_mSO_3H$; where m is a value between 1 and 30.

A particularly suitable material is:

where m is a value between 1 and 30 and M is Zr or Ti.

The above materials may be used alone or supported on known catalyst supports and, in either event, may optionally be used in conjunction with one or more Lewis acids.

DESCRIPTION OF THE INVENTION

This invention broadly is an acid-catalyzed process, using solid acid catalysts, for producing certain trialkylacetic acids from corresponding branched olefins, carbon monoxide, and water according to the following reaction:

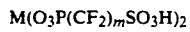

where $R^1$, $R^2$ = H, alkyl, or substituted alkyl; $R^3$, $R^4$ = H, alkyl, or substituted alkyl; if $R^1$ and $R^3$ are H, then $R^2$ and $R^4$ must be alkyl or substituted alkyl and at least one of $R^2$ and $R^4$ must be branched. Each of $R^1$, $R^2$, $R^3$, and $R^4$ may be the same or different than the other substituent moieties. Preferably, $R^1$ and $R^2$ are independently $C_{1-5}$ linear or branched alkyl groups possibly substituted with inorganic moieties such as Si, N, P, or S which do not tend to form ionic species in the water-containing reaction medium. Most preferred, in the sense that pivalic acid is the product, is the situation in which $R^1$ and $R^2$ are —$CH_3$ and $R^4$ and $R^3$ are H.

This invention also includes the specific overall process of producing pivalic acid from isobutene, carbon monoxide, and water:

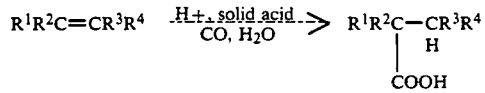

Solid Acid Catalysts

The solid acid catalysts used in the is process may be any of a set of materials known as Molecular Engineered Layered Structures ("MELS"). In particular, the acid catalyst comprises a compound comprising sulfonic acid and phosphonic acid groups in which the phosphonic acid groups are covalently bonded to a polymeric chain, where the resulting product is represented by the general formula:

$$M(O_3ZR)_n$$

where M is a tetravalent metal ion, Z is a pentavalent atom selected from the elements of Group V having atomic weights greater than 30, R is selected from substituted and unsubstituted organo radicals and mixtures of organo radicals and hydrogen radicals, and n varies from 1 to 2. Desirably, M is selected form the group selected from Zr, W, U, Ti, Th, Te, Sn, Si, Ru, Pu, V, Pr, Pb, Os, Nb, Mo, Mn, Ir, Hf, Ge, Ce, and mixtures thereof and Z is P. More desirably, Z is P and M is Zr or Ti.

The R moiety may be selected from substituted or unsubstituted alkyl, aryl, and mixtures of alkyl, aryl, hydrogen, and hydroxyl radicals. The substituents of the "R" moiety may be fluorien, chlorine, bromine, iodine, or the like as well as sulfur, oxygen, or phosphorus. Particularly desirable "R" moieties include—$(CH_2)_mSO_3H$, —$C_6H_4SO_3H$,—$C_6H_4(SO_3H)_2$, —$(CF_2)_mSO_3$; where m is a value between 1 and 30.

A particularly suitable material is:

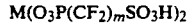

where m is a value between 1 and 30 and M is Zr or Ti.

The MELS materials useful as the catalysts in the process may be prepared according to the procedures described in U.S. Pat. Nos. 4,232,146; 4,235,990; 4,235,991; 4,256,872; 4,267,308; 4,276,409; 4,276,410; 4,276,411; 4,298,723; 4,299,943; 4,373,079; 4,384,981; 4,386,013; 4,390,690; 4,429,111; 4,436,899; and 4,868,343

(all of which are incorporated by reference) by reacting an organophosphonic acid or organophosphonate substituted, pentavalent atom-containing acid or, the polymeric chain may be formed, first, by the same procedures and subsequently sulfonated to provide the sulfonic acid groups. In any case, the polymer may be prepared having a layered structure similar to the layered structure of zirconium phosphate.

The above materials may be used alone or supported on known catalyst supports and, in either event, may optionally be used in conjunction with one or more Lewis acids.

Lewis Acids

The catalyst system used in this process comprises one or more of the MELS materials discussed above and may also comprise one or more Lewis acids.

A Lewis acid is a molecule which can form another molecule or an ion by forming a complex in which it accepts two electrons from a second molecule or ion. Typical strong Lewis acids include boron halides such as $BF_3$, $BCl_3$, $BBr_3$, and $BI_3$; antimony pentafluoride ($SbF_5$); aluminum halides ($AlCl_3$ and $AlBr_3$); titanium halides such as $TiBr_4$, $TiCl_4$, and $TiCl_3$; zirconium tetrachloride ($ZrCl_4$); phosphorus pentafluoride ($PF_5$); iron halides such as $FeCl_3$ and $FeBr_3$; and the like. Weaker Lewis acids such as tin, indium, bismuth, zinc, or mercury halides are also acceptable. Preferred Lewis acids are $SbF_5$, $AlCl_3$, and $BF_3$; most preferred is $BF_3$. If $BF_3$ or other gaseous Lewis acid is selected, it may be added along with the carbon monoxide reactant in a gaseous form to the reaction medium. Solid Lewis acids may be comminuted and added to the MELS materials to produce a mixture which may, in turn, be added to the reaction mixture. It should be apparent that some selection of Lewis acid from this list is necessary depending upon such factors as the amount of water present, the trialkylacetic acid desired, etc. since there will be a tendency for the Lewis acid to hydrolyze in competition with the reaction forming the carboxylic acid.

In contrast to prior art processes, Lewis acids such as $BF_3$ are present in amounts substantially less than a molar equivalent to the branched olefin.

Reaction Conditions

The Lewis acid, water, and the carbon monoxide may be added in convenient forms (gas, liquid, or solid) to the reaction medium. Some care should be exercised in contacting the water reactant and the Lewis acid, e.g., the Lewis acid desirably is not initially placed in contact with the water but the water is instead added last to the medium. In contrast to prior art processes, the Lewis acid is present in amounts substantially less than a molar equivalent to the branched olefin. Isobutene or other branched olefins are added to the reactor with the required water. The reaction is more facile at elevated temperature, e.g., at 65° C. or higher, but a which the reaction medium is till in the liquid phase. Excellent results have been achieved at temperatures between 100° C. and 150° C. A temperature of about 125° C. is most preferred.

The process may be operated using one or more solvents as the reaction medium. Solvents such as linear or cyclic alkanes are desirable in that they are unreactive and are often easily separated from the product organic acids. Materials such as isobutane are especially desirable because they are readily separable from products such as pivallic acid, e.g., isobutane (bp. −12° C.) may be removed from the product pivalic acid (bp. 163° C.) by flashing. Further, it dissolves both the isobutene reactant and is generally unreactive toward the Lewis acid catalyst adjunct.

The invention has been disclosed by direct description. Below may be found a number of examples showing various aspects of the invention. The examples are only examples of the invention and are not to be used to limit the scope of the invention in any way.

EXAMPLES

The following Examples show the synthesis of pivalic acid from isobutene and the benefits of the catalyst system. In each example, a sample of the MELS catalyst was added to a 300 ml autoclave. The autoclave was then evacuated and pressurized with boron trifluoride. The isobutane solvent was then added and the stirrer started. The autoclave was pressurized to about 1200 psi with carbon monoxide and heated to the reaction temperature. Isobutene reactant (dissolved in isobutane solvent) was co-added with water.

EXAMPLE 1

MELS Catalyst Preparation

An amount of fumed silica (45.5 g) was treated with 91 ml of an aqueous solution containing 20.3 g of $(HO)_2P(O)CF_2SO_3H$. The product was dried at 100° C. overnight. The dried product was treated with a solution containing 15.4 g of $ZrOCl_2H_2O$ diluted to 65.5 ml with water. This product was dried overnight at 110° C. to give a catalyst powder containing 35% $Zr(O_3PCF_2SO_3H)_2$.

EXAMPLE 2

Pivalic Acid Production with Zr–MELS/SiO$_2$

This example shows the use of a preferred catalyst system to produce pivalic acid.

A five gram amount of Example 1 catalyst was added to the reactor. The autoclave was pressured to ten psi of boron trifluoride and to 1260 psig total. The autoclave was then heated to 95° C. After flashing, the product contained about 67% pivalic acid.

EXAMPLE 3

MELS Catalyst Re-use

The procedure of Example 2 was repeated re-using the MELS catalyst of that Example. The entire contents of the autoclave (except the MELS catalyst) was flushed using isobutane. The autoclave was re-pressured with ten psi of boron trifluoride. The reactants were added. The catalyst showed no diminution of activity during the repetition.

EXAMPLE 4

Demonstration at 125° C.

This example (and Example 5) show that the process operates well at higher temperatures.

The procedure of Example 2 was repeated five times using the same sample of MELS catalyst but with a fresh introduction of 65 psi of $BF_3$ added each time. The reaction temperature was 125° C. The yields of pivalic acid (as compared to moles of isobutene feed) in the isolated product varied between 78% and 90%.

EXAMPLE 5

Demonstration at 140° C.

The procedure of Example 4 was repeated once at 140° C. The isolated product contained 90% pivalic acid.

EXAMPLE 6

Pivalic Acid Production with Ti-MELS/SiO$_2$

This example shows the use of a preferred catalyst system to produce pivalic acid.

A five gram amount of a titanium containing analog to the Example 1 catalyst was added to the reactor. The autoclave was pressured to 65 psi of boron trifluoride and to 1260 psig total. The autoclave was then heated to 125° C. to 135° C. After flashing, the product contained more than about 70% pivalic acid.

COMPARATIVE EXAMPLE 1

This comparative example shows the use of MELS catalyst along (i.e., without BF$_3$) and its lower productivity in producing pivalic acid.

The amount of MELS catalyst added to the reactor was five grams and the reaction temperature was 95° C. Pivalic acid was produced as a minor component (approximately 17% of the product) with the balance of the product being dimers and trimers.

This invention has been described using examples to show preferred embodiments. It will be apparent to those skilled in the art that modifications and changes may be made which still fall within the spirit and scope of the attached claims.

We claim as our invention:

1. A process for the production of trialkylacetic acids comprising the steps of:
   a. contacting a branched olefin of the formula:

$$R^1R^2C=CR^3R^4$$

where $R^1$, $R^2$ are H or $C_1$-$C_5$ alkyl and $R^3$, $R^4$ are H or $C_1$-$C_5$ alkyl (if $R^1$ and $R^3$ are H, then $R^2$ and $R^4$ must be alkyl and at least one of $R^2$ and $R^4$ must be branched) with carbon monoxide and a catalytic amount of a catalyst system comprising one or more solid acids comprising sulfonic acid and phosphonic acid groups and in which the phosphonic acid groups are covalently bonded to a polymeric chain represented by the general formula:

$$M(O_3ZR)_n$$

where M is a tetravalent metal ion selected from Zr, W, U, Ti, Th, te, Sn, Si, Ru, Pu, V, Pr, Pb, Os, Nb, Mo, Mn, Ir, Hf, Ge, and Ce, Z is a pentavalent atom selected from the elements of Group V having atomic weights greater than 30, R is selected from substituted and unsubstituted organic radicals and mixtures of substituted and unsubstituted organic radicals and n varies from 1 to 2 under conditions suitable for the production of trialkylacetic acids of the formula:

$$\begin{array}{c}R^1R^2C-CHR^3R^4\\|\\COOH\end{array}$$

and containing a molar amount of a Lewis acid less than the amount of branched olefin, and then with an amount of water stoichiometric for the branched olefin, and
   b. recovering the trialkylacetic acid.

2. The process of claim 1 where R is selected from —(CH$_2$)$_m$SO$_3$H, —C$_6$H$_4$SO$_3$H, —C$_6$H$_4$(SO$_3$H)$_2$, —(CF$_2$)$_m$SO$_3$H and where m is a value between 1 and 30.

3. The process of claim 1 in which the catalyst is represented by:

$$M(O_3P(CF_2)_mSO_3H)_2$$

where m is 1 to 30 and M is Zr or Ti.

4. The process of claim 3 where the catalyst system comprises a material represented by:

$$Zr(O_3P(CF_2)_mSO_3H)_2$$

where m is 1 to 30.

5. The process of claim 1 where the catalyst additionally comprises one or more Lewis acids chosen from BF$_3$, BCl$_3$, BBr$_3$, BI$_3$, SbF$_5$, AlCl$_3$, AlBr$_3$, TiBr$_4$, TiCl$_4$, TiCl$_3$, ZrCl$_4$, PF$_5$, FeCl$_3$, and FeBr$_3$.

6. The process of claim 2 where the catalyst additionally comprises one or more Lewis acids chosen from BF$_3$, BCl$_3$, BBr$_3$, BI$_3$, SbF$_5$, AlCl$_3$, AlBr$_3$, TiBr$_4$, TiCl$_4$, TiCl$_3$, ZrCl$_4$, PF$_5$, FeCl$_3$, and FeBr$_3$.

7. The process of claim 5 where the catalyst system additionally comprises one or more Lewis acids chosen from SbF$_5$, AlCl$_3$, and BF$_3$.

8. The process of claim 7 where the Lewis acid is BF$_3$.

9. The process of claim 1 where $R^1$ and $R^2$ are independently $C_{1-5}$ linear or branched alkyl groups.

10. The process of claim 9 where $R^1$ and $R^2$ are —CH$_3$ and $R^3$ and $R^4$ are H.

11. The process of claim 10 where the catalyst system additionally comprises one or more Lewis acids chosen from SbF$_5$, AlCl$_3$, and BF$_3$.

12. The process of claim 11 where the Lewis acid is BF$_3$.

13. A process for the production of pivalic acid comprising the steps of
   a. contacting isobutene and carbon monoxide with a catalyst system comprising a material which is represented by:

$$M(O_3P(CF_2)_mSO_3H)_2$$

where m=1 to 30 and M=Zr, Ti and containing a molar amount of Lewis acid less than the amount of isobutene, and then with an amount of water stoichiometric to the isobutene, and
   b. recovering the pivalic acid.

14. The process of claim 13 where the catalyst system comprises one or more Lewis acids chose from SbF$_5$, AlCl$_3$, and BF$_3$.

15. The process of claim 14 where the catalyst system comprises a material represented by:

$$Zr(O_3P(CF_2)_mSO_3H)_2$$

where n is between 1 and 30.

16. The process of claim 15 where the Lewis acid is BF$_3$.

17. A process for the production of trialkylacetic acids comprising the steps of:
   a. contacting a branched olefin of the formula:

$$R^1R^2C=CR^3R^4$$

where $R^1$, $R^2$ are H or $C_1$–$C_5$ alkyl and $R^3$, $R^4$ are H or $C_1$–$C_5$ alkyl (if $R^1$ and $R^3$ are H, then $R^2$ and $R^4$ must be alkyl or substituted alkyl and at least one of $R^2$ and $R^4$ must be branched) with carbon monoxide and a catalytic amount of a catalyst system comprising one or more solid acids comprising sulfonic acid and phosphonic acid groups and in which the phosphonic acid groups are covalently bonded to a polymeric chain represented by the general formula:

$$M(O_3ZR)_n$$

where M is selected from Zr, W, U, Ti, Th, Te, Sn, Si, Ru, Pu, V, Pr, Pb, Os, Nb, Mo, Mn, Ir, Hf, Ge, Ce, and mixtures thereof, Z is P, R is selected from $(CH_2)_mSO_3H_1$ —$C_6H_4SO_3H_1$ —$C_6H_4(SO_3H)_2$, —$(CF_2)_mSO_3$; where m is a value between 1 and 30, and n varies from 1 to 2 so to produce trialkylacetic acids of the formula:

$$\begin{array}{c} R^1R^2C-CHR^3R^4 \\ | \\ COOH \end{array}$$

and containing a molar amount of a Lewis acid less than the amount of branched olefin, and then with an amount of water stoichiometric to the branched olefin, and b. recovering the trialkylacetic acid.

* * * * *

UNITED STATES PATENT AND TRADEMARK OFFICE
CERTIFICATE OF CORRECTION

PATENT NO. : 5,241,112

DATED : August 31, 1993

INVENTOR(S) : Sanderson et al.

It is certified that error appears in the above-identified patent and that said Letters Patent is hereby corrected as shown below:

In column 7, at line 53, please change "te" to --Te--.

In column 8, at line 62, please change "where n is" to --where m is--.

In column 10, at lines 2-3, please change

"$(CH_2)_m SO_3 H_1 \quad —C_6H_4SO_3H_1 \quad —C_6H_4(SO_3H)_2, \quad —(CF_2)_m SO_3;$" to --$(CH_2)_m SO_3H, \quad —C_6H_4SO_3H, \quad —C_6H_4(SO_3H)_2, \quad —(CF_2)_m SO_3H$--.

Signed and Sealed this

Twelfth Day of July, 1994

Attest:

BRUCE LEHMAN

*Attesting Officer*     *Commissioner of Patents and Trademarks*